United States Patent [19]

Guirguis et al.

[11] Patent Number: 6,149,871
[45] Date of Patent: Nov. 21, 2000

[54] SYSTEM FOR PROCESSING MULTIPLE SPECIMENS OF BIOLOGICAL FLUID

[75] Inventors: Amin A. Guirguis, Alexandria, Egypt; Raouf A. Guirguis, Vienna, Va.

[73] Assignee: LaMina, Inc., Herndon, Va.

[21] Appl. No.: 09/042,005

[22] Filed: Mar. 13, 1998

Related U.S. Application Data

[60] Provisional application No. 60/056,445, Aug. 25, 1997.

[51] Int. Cl.$^7$ ............................................. B01D 29/00
[52] U.S. Cl. ........................... 422/101; 210/260; 210/261
[58] Field of Search ........................... 422/63, 101, 103, 422/104; 210/240, 241, 473, 260, 261; 435/288.4, 288.5, 297.2; 436/177

[56] References Cited

U.S. PATENT DOCUMENTS

| | | | |
|---|---|---|---|
| 536,552 | 3/1895 | Swift | 359/391 |
| 3,722,502 | 3/1973 | Besuner et al. | 600/575 |
| 3,774,455 | 11/1973 | Seidler | 73/444 |
| 3,851,972 | 12/1974 | Smith et al. | 356/72 |
| 4,040,791 | 8/1977 | Kuntz | 422/102 |
| 4,167,875 | 9/1979 | Meakin | 422/101 X |
| 4,170,056 | 10/1979 | Meyst et al. | 29/896.62 |
| 4,346,057 | 8/1982 | Bowser | 422/101 |
| 4,395,493 | 7/1983 | Zahniser | 435/286.4 |
| 4,427,415 | 1/1984 | Cleveland | 422/101 X |
| 4,435,507 | 3/1984 | Stenkvist | 435/262 |
| 4,473,530 | 9/1984 | Villareal | 422/58 |
| 4,557,274 | 12/1985 | Cawood | 600/573 |

(List continued on next page.)

FOREIGN PATENT DOCUMENTS

| | | | |
|---|---|---|---|
| 0503128 | 9/1992 | European Pat. Off. | |
| 58-216960 | 12/1983 | Japan | 422/63 |
| 62-113062 | 5/1987 | Japan | 422/101 |
| 2019242 | 10/1979 | United Kingdom | 422/101 |

OTHER PUBLICATIONS

Jacalyn L. Papillo et al. B.S., CT (ASCP), Cell Recovery: ThinPrep Method vs. Cytocentrifugatio.

Martha Hutchinson, Ph.D., M.D. et al., A Study of Cell Loss in the Conventional Pap Smear.

Katherine K. Mul et al., CT (ASCP), The ThinPrep Sample Preparation Process–A Matter of Reproducibility.

G.H. Green et al., Nuclepore Membrane Filter Techniques for Diagnostic Cytology of Urine and Other Body Fluids, Medical Laboratiory Technology, 30: 265–271 (1973).

Diagnostic Cytology, Nuclepore Corporation, 1–13.

The ThinPrep Processor and The CDS 1000 Cytology Work Station, Cytce Corporation, 1–21.

Goran Ocklind, Optically Eliminating The Visible Outlines Of Pores In Intact Polycarbonate (Nuclepore) Filters, ACTA Cytological, 31: 946–949 (1987).

Wartio VAARA et al., Nature, 238: 407–408 (1972).

James Robb, M.D. et al, Diagnostic Cytopathology, 14: 305–309 (1996).

James Linder, M.D., Arch Pathol Lab Med, 121: 282–286 (1997).

*Primary Examiner*—Mark Spisich
*Attorney, Agent, or Firm*—Foley & Lardner

[57] ABSTRACT

Apparatus for processing multiple units of a particulate matter-containing fluid in independent source containers. Each source container has a separate filter assembly associated therewith near the top of the container, and the filter assemblies are in fluid communication with a manifold. Fluid is moved upwardly through the filter assemblies, out of the source containers and into a manifold assembly. Movable platforms, including a slide-carrying platform, support and manipulate the components such that the particulate matter samples are transferred from the filters to the slides.

12 Claims, 7 Drawing Sheets

U.S. PATENT DOCUMENTS

| | | | |
|---|---|---|---|
| 4,573,983 | 3/1986 | Annis | 604/322 |
| 4,609,264 | 9/1986 | Podvin et al. | 359/393 |
| 4,642,220 | 2/1987 | Bjorkman | 435/288.4 X |
| 4,685,472 | 8/1987 | Muto | 600/573 |
| 4,787,988 | 11/1988 | Bertoncini et al. | 422/101 X |
| 4,810,471 | 3/1989 | Wachob et al. | 422/101 X |
| 4,827,944 | 5/1989 | Nugent | 600/584 |
| 4,917,804 | 4/1990 | Franks et al. | 422/101 X |
| 4,948,564 | 8/1990 | Root et al. | 422/101 |
| 4,960,130 | 10/1990 | Guirguis | 600/573 |
| 5,022,411 | 6/1991 | Guirguis | 600/584 |
| 5,038,793 | 8/1991 | Guirguis | 600/573 |
| 5,077,012 | 12/1991 | Guirguis | 422/58 |
| 5,143,627 | 9/1992 | Lapidus et al. | 210/767 |
| 5,380,437 | 1/1995 | Bertoncini | 422/101 X |
| 5,496,473 | 3/1996 | Chow | 422/101 X |
| 5,846,493 | 12/1998 | Bankier et al. | 422/101 |

SYSTEM FOR PROCESSING MULTIPLE SPECIMENS OF BIOLOGICAL FLUID

This application claims the benefit of provisional application No. 60/056,445, filed Aug. 25, 1997.

TECHNICAL FIELD

This invention relates to a system, apparatus, and method for processing separate containers of biological fluid.

BACKGROUND OF THE INVENTION

In a wide variety of technologies, the ability and/or facility in separating matter, typically particulate matter, from a fluid is a critical component in the ability to test for the presence of substances in the fluid. Too often, interference associated with sample preparation obscures the target cells to such a degree that the process is not sufficiently reliable, or too costly.

A similar scenario applies to many other fields which involve detection and/or diagnosis, including environmental testing, radiation research, cancer screening, cytological examination, microbiological testing, and hazardous waste contamination, to name just a few.

All that is required for a cytological examination of a sample is that a sample of cells be obtained from the patient, which can typically be done by scraping or swabbing an area, as in the case of cervical samples, or by collecting body fluids, such as those obtained from the chest cavity, bladder, or spinal canal, or by fine needle aspiration. In a conventional manual cytological examination, the cells in the fluid of an individual specimen are then transferred onto a glass slide for viewing. A limiting factor in the sample preparation protocol is adequately separating solid matter from its fluid carrier (e.g., a variety of fluids, such as physiological, biological and environmental), and in easily and efficiently collecting and concentrating the solid matter in a form readily accessible to microscopic examination. There is also a significant limitation in how many specimens can be processed at the same time, or how many specimens can be processed in a day.

Furthermore, prompt processing of urine to obtain fresh cells traditionally has been recommended to ensure the accuracy of quantitative culture results, urinalysis and microscopy. Fresh cells tend to stick to a glass slide much better than cells from preserved urine, allowing for smoother cell spread onto the glass body. Delays in processing, negligent care in either inpatient or outpatient settings and lack of refrigeration may lead to non-optimal slide preparation. One known solution to the delay problem is the use of chemical preservatives with the urine. The presence of liquid preservatives, however, in the urine specimen raises the specific gravity of the specimen to unmeasurable levels and may limit the potential usefulness of the urine for various types of traditional quantitative analysis, such as slide microscopy.

A number of urine or other biological fluid specimen containers have been developed to allow liquid biological specimens to be tested without removing the lid of the urine or biological fluid container. None of the prior art solves the problem of transferring cells in a monolayer to a slide for examination without submerging portions of the device in the sample (and increasing contamination), consistently and repeatedly forming a high quality monolayer on the microscope slide, and processing the sample so that the fluid from which the cells were taken is preserved.

Currently, body fluid samples are collected for cytological examinations using special containers. These containers usually contain a preservative solution for preserving the cytology specimen during shipment from the collection site to the cytology laboratory. Furthermore, cytology specimens collected from the body cavities using a swab, smear, flush or brush are also preserved in special containers with fixatives (e.g., alcohol or acetone fixatives) prior to transferring cells onto the slide or membrane for staining or examination.

Diagnostic microbiology and/or cytology, particularly in the area of clinical pathology, bases diagnoses on a microscopic examination of cells and other microscopic analyses. The accuracy of the diagnosis and the preparation of optimally interpretable specimens typically depends upon adequate sample preparation. New methodologies such as immunocytochemistry and image analysis require preparations that are reproducible, fast, biohazard-free and inexpensive. Different cell preparation techniques of the present invention address the issues of non-uniform cell densities, uneven cell distribution and air drying artifact. These preparations have resulted in an even distribution of cells that have superior morphology, which has improved light microscopic visualization and has allowed for the use of image cytometry instruments. The solid matter preparation techniques of the present invention address the issues of non-uniform matter densities, uneven matter distribution, and sample loss due to the number of steps involved in the sample preparation. The preparations of the present invention result in an even distribution of solids that have superior morphology, improved visualization, and are readily positioned and available for light absorbance analysis without the need to further manipulate or prepare the sample.

In view of this, there is a growing need for a system and method for economically and efficiently processing multiple samples of a fluid, such as a biological fluid.

SUMMARY OF THE INVENTION

Processes and systems according to the invention include a manifold assembly for processing multiple specimens of biological fluid, preferably in a simultaneous or sequential manner. Processes and systems according to the invention may also include a plurality of relatively movable platforms for supporting and manipulating various components of system.

The present invention relates to an apparatus and method for collecting multiple individual containers of matter for detection, analysis, quantification, and/or visualization, and processing multiple containers during a single processing session. The devices and methods of the present invention are particularly suitable for separating matter from biological, physiological, and environmental fluids and presenting the particulate matter in an improved manner for cytological examination.

The present invention also relates to a manifold apparatus and method for collecting a uniform layer of cells from urine or other fluid specimen in a cytology collection apparatus or assay module, a portion of which can be removably detached from the collection container for application to a slide. An apparatus according to the invention resolves problems associated with known equipment for collecting cells and other particles for cytology by providing a mechanism of relatively simple structure and operation that separates particles from a liquid solution, collects an approximately known quantity of the cells in a monolayer, and transfers the collected cells to a microscope slide. In some embodiments of the invention, no element of the apparatus is placed in the liquid sample, thus preventing unnecessary contamination of the sample. In all embodiments of the invention, the particulate matter in the sample is collected on a collection site by using two fluid flow paths to pass the liquid sample through a filter to remove the desired cells.

The present invention also relates to a cell collection and distribution apparatus capable of processing multiple specimens, and which can be easily disassembled to allow face to face transfer of cells from the device to a slide for microscope examination. The present invention provides an improved apparatus and method for collecting a monolayer of cells which can be transferred to a microscope slide.

The devices of the present invention obviate the need for a trained technician to properly prepare multiple sample substrates. Thus, time, expense, and expertise are eliminated or reduced as critical factors in sample preparation protocols.

The devices and methods of the present invention also provide advantages in sample preparation because they are suitable for use with fresh, untreated cells, unmodified cells, and are particularly designed to provide a thin, uniform layer of solid matter (up to approximately 40 microns or more). This invention is particularly useful for collecting cells for a pap smear.

According to another aspect of the present invention, the matter collection apparatus may also include additional modules, removable or integrated, for treating the fluid. For example, the fluid may be treated with a matter collection module, in combination with a debris removal module, a chromatography module, an assay module, or combinations of these and other devices. These and other modules or treatment protocols provide features which may be desirable to incorporate into a sample preparation apparatus according to the invention.

For example, the devices and methods of the present invention have many advantages for conventional microbiology and hematology. The collected cells are in a predetermined area easily accessible for visual examination, to a radiant light source, and/or to a wavelength absorbence meter. Because cells are concentrated in a single layer, they are almost always in one focal plane, thus eliminating or reducing interference by other particles and virtually eliminating technician time and expertise in establishing a proper reading. The minimal matter overlap achieved ensures that all matter can be easily examined with little chance for critical solids to be obscured by clumps of overlapping solids or debris. The apparatuses of the present invention even permit the use of automated devices to detect and analyze any solid matter in a given population. It also permits a detailed analysis of the chemical composition of the matter.

The effectiveness of transferring the monolayer cells from the filter to a microscope slide has proven to be very high without differential cell loss. Microscopic examination shows that the cell distribution is the same on the slide as on the filter.

In a preferred embodiment of the invention, the manifold apparatus includes a platform having a plurality of filter assemblies, a platform for positioning a plurality of specimen containers, a platform for positioning a plurality of microscope slides and/or filters, and a control system for operating, monitoring, and sequencing the various assemblies. In accordance with the invention, the apparatus includes a manifold assembly for processing multiple specimens simultaneously or sequentially. The manifold assembly includes a network of conduits with a series of individual conduits in fluid communication with an individual filter assembly, an intermediate series of conduits that conduct the specimen from multiple filter assemblies, and a single conduit for conducting all of the specimens from all of the filter assemblies.

A manifold apparatus according to the invention may be a manual system, a semi-automated system, or a fully automated system. The semi-automated and automated system may include one or more control systems for defining and controlling one or more facets of the operation of the apparatus.

For example, the control system monitors the particulate matter collecting operation by monitoring parameters of the liquid flow to determine when a pre-determined quantity of particulate is collected on the filter. The control system may also position an upper assembly of the apparatus (containing a filter assembly) for abutment against a microscope slide.

It is important to the method and apparatus of the invention that the cells maintain the monolayer distribution with which they were collected on the filter as the cells are transferred from the filter device to the microscope slide. The invention thus provides cell collection and transfer means that produce a monolayer of cells on the microscope slide.

An instrument according to the present invention preferably employs a fresh sample vial, an unused filter assembly, and an unused microscope slide for each individual cell specimen. Moreover, the relatively simple operation, and the multiple functions which the instrument performs, minimize the requirements for operator attendance and time, as well as minimizing maintenance and preparation.

A preferred embodiment of the invention may include multiple subassemblies so that a preferred automated apparatus according to the invention can process at least two, typically five or more, specimens simultaneously or sequentially.

Additionally, processes and systems according to the invention may include a gas inlet and/or a gas outlet that maximizes the recovery of a biological fluid that may be entrapped or retained during processing; the processes and systems may also include a drip chamber that collects gas and/or controls the rate of flow of a biological fluid through the system.

The accompanying drawings show illustrative embodiments of the invention from which these and other of the objectives, novel features and advantages will be readily apparent.

BRIEF DESCRIPTION OF THE DRAWINGS

FIG. 4A-1 is vertical sectional view through the top portion of a filter assembly;

FIG. 4A-2 is a bottom plan view of the filter assembly of FIG. 4A-1;

FIG. 4B-1 is a vertical sectional view through the bottom portion of a filter assembly;

FIG. 4B-2 is a top plan view of the filter assembly of FIG. 4B-1;

SPECIFIC DESCRIPTION OF THE INVENTION

Figure 1:
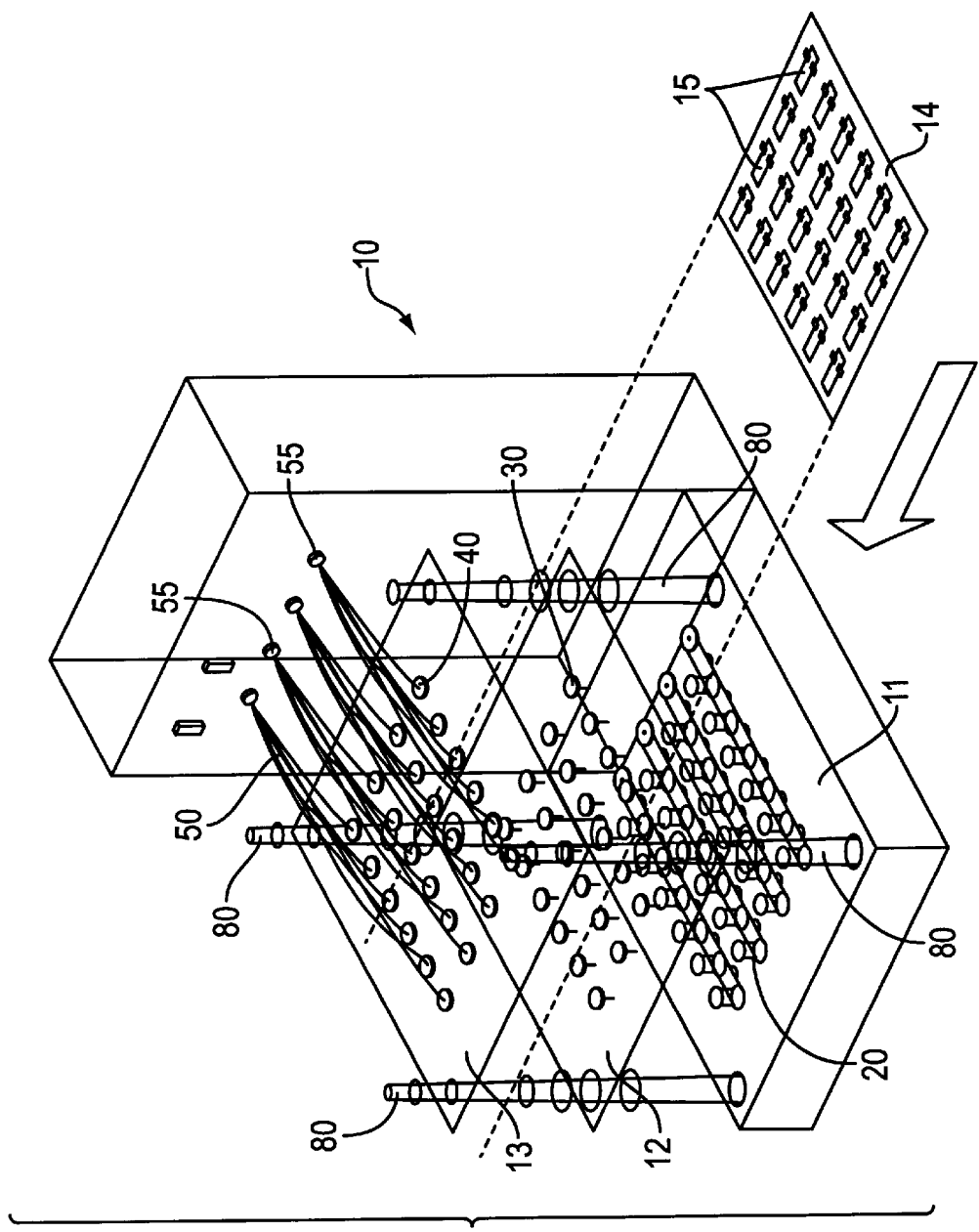
FIG. 1 is a perspective view of one embodiment of a biological fluid processing system comprising a manifold assembly according to the invention.

The present invention includes an apparatus for preparing multiple samples of one or more particulate matter-containing fluids for diagnostic examination, preferably microscopic examination. The present invention also includes an apparatus for separating particulate matter from one or more fluids simultaneously or sequentially. The present invention also includes a manifold assembly comprising a series of conduits configured to process one or more fluids simultaneously or sequentially.

The present invention also includes a method for preparing multiple samples of one or more particulate matter-containing fluids for diagnostic examination wherein multiple samples of fluid are passed through a manifold assembly. The present invention also includes a method for separating particulate matter from a fluid by passing the fluid through a manifold assembly configured to process multiple samples of fluid simultaneously or sequentially. The present invention also includes a method for preparing particulate matter for visual examination by passing individual samples of a fluid containing particulate matter through a filter assembly, passing multiple samples of the fluid through a manifold assembly, and contacting a portion of the filter assembly to one or more elements suitable for or designed for diagnostic examination, e.g., a microscope slide or an infra red scanner.

In accordance with the present invention, particulate matter-containing fluid, such as a biological fluid, in separate source containers is passed through a biological fluid processing or manifold system that separates the particulate matter from the fluid and collects the particulate matter in a manner suitable for diagnostic testing and/or visual examination.

The present invention also includes devices and methods for collecting fluids, such as biological, physiological, or environmental fluids, removing predetermined matter from the fluid, without centrifugation, and diagnosing and testing the matter.

In accordance with the invention, a variety of elements, structures, and assemblies are configured to process one or more particulate matter-containing fluids. Typical elements and structures include but are not limited to one or more collection containers; one or more filter assemblies configured to remove particulate matter from a fluid, said assembly being configured to engage a collection container and/or the fluid in the collection container; one or more covers configured to engage a filter assembly housing; and a plurality of conduits, with individual conduits adapted to engage individual covers, said plurality of conduits configured to process multiple individual samples of fluid simultaneously or sequentially. As will be disclosed in more detail below, an apparatus according to the invention may also include a wide variety of other elements and structures as desired.

As used herein, multiple specimens or multiple samples refers to more than one individual particulate matter-containing fluid sample or specimen. Prior to removal of any particulate matter from the fluid, it is intended that multiple specimens refers to individual separate samples, i.e., neither the fluid nor the particulate matter from individual samples is commingled. After removal of particulate matter from the fluid, it is intended that multiple specimens refers to either individual samples or may refer to commingled fluids from more than one processed sample.

As used herein simultaneously or sequentially refers to the temporal sequence of processing as those words are normally defined, and is intended to conceptually include that processing or portions of the process occur as a batch. It is further intended to conceptually include that individual process steps for individual specimens occur close enough in time that they may be considered to occur in the same overall processing session. It is also intended that both simultaneously and sequentially are defined with the understanding that at some point of the process, fluids or fluid flow paths combine. In this sense, this aspect of the invention is intended to differentiate the present invention from an apparatus that processes multiple samples merely as a combination of more than one individual and separate flow path.

As used herein, manifold or manifold assembly refers to the various structures that comprise a fluid flow path wherein at some point on the flow path fluid from more than one specimen combines or mixes. As will be evident to one skilled in the art, manifold is used in its normal definition and is intended to reflect the wide range of structures, conduits, assemblies, and the like that can be used to reduce multiple flow paths to a lower number of flow paths. This definition is intended to differentiate the present invention from devices that process a single separate specimen through completion or devices that process multiple specimens without any commingling of fluids at any point in the processing.

A manifold apparatus according to the invention may be a wholly manual apparatus, or may be semi-automated or fully automated. One skilled in the art will readily recognize that different apparatus elements and different methods of operation may be used or substituted depending on the level of automation incorporated or desired in a specific apparatus.

An apparatus according to the present invention is a collection of assemblies, structures, and/or mechanisms for removing particulate matter from a liquid and transferring the particulate matter to a microscope slide or other cytological examination element from a multiplicity of source containers. During operation of the apparatus processing the fluid to remove particulate matter from the fluid may include or involve one or more of the following stages or steps: removing the sample container cover used to ship or transport the sample container to the site of the manifold apparatus; providing a conduit or other fluid flow channels for passing a portion of the particulate containing liquid through the filter assembly to a disposal region or container; providing a microscope slide movable to a position adjacent to, aligned with, and/or resting against a portion of the filter assembly; one or more subassemblies for replacing the used filter assembly with an unused filter assembly; a belt communicating with a portion of the filter assembly loader for rotating the portion; one or more transport mechanisms for moving and/or positioning one of the structures noted above; one or more carriages for retaining, positioning, or moving one or more of the structures noted above; one or more motors for moving or positioning one or more of the structures noted above; and one or more control systems for operating, preferably selectively and/or sequentially, one or more of the various structures noted above.

The present invention also involves a method for processing a liquid containing particulate matter using a manifold apparatus configured according to the invention. The present invention also involves removing particulate matter from a liquid and collecting the particulate matter on a medium suitable for cytological examination of the particulate matter.

As used herein, fluid refers to any liquid for which it may be desirable to collect a component of the liquid for the purpose of establishing its identity or presence in the liquid. Typically, the component in the liquid will be a solid matter, such as particulate matter. For example, the fluid may be air or gas, or a biological fluid, such as urine, and it may be desirable to determine the presence of cancer cells or certain proteins in the biological fluid. In another example, it may be desirable to evaluate the nature of contaminants, such as molecular contaminants, in ultra-pure water used in the electronics industry. Other exemplary fluids include but are not limited to body fluids, such as blood, spinal fluid, or amniotic fluid; bronchial lavage; sputum; fine needle aspirates; ground water; industrial processing fluids; electronic or medical dialysis fluids; to identify just a few. It is intended that the invention should not be limited by the type of fluid being processed.

As used herein, particulate matter refers to any substance in a fluid which is capable of collection and evaluation, preferably by cytological examination. Exemplary matter includes, but is not limited to cells or cell fragments, proteins, molecules, polymers, rubbers, stabilizers, antioxidants, accelerators, silicones, alkyds, thiokols, paraffins, thermoplastics, bacteria, pesticides, and herbicides. Specific exemplary polymeric matter include, but is not limited to polyethylene, polypropylene, polyisobutylene, polyacrylonitrile, polyethylene glycol, polyvinylchloride, polystyrene, polysulfide, polymethylmethacrylates, polyethyleneterephthalates, bisphenol A (a common environmental contaminant), ethyl cellulose, nitrocellulose, polyurethane, and nylon. Specific exemplary biological matter includes cancer cells, including distinguishing between metastatic and normal cancer cells; proteins, nucleic acids, antibodies, or the like. It is intended that the invention should not be limited by the type of matter being processed.

As used herein, adapted for communication, communicating, or similar terms refer to any means, structures, or methods for establishing fluid flow through the system, as are well known by practitioners in the art. Exemplary structures are shown in the Figures. For example, a conduit may have a connector adapted to receive or connect to a mated connector on another conduit. As used herein, connector refers to any structure used to form a joint or to join itself to another piece. These connectors or connections establish a fluid flow path through various elements of the apparatus, assembly, or system. Typical connections include but are not limited to mating connections, such as Luer-type, screw-type, friction-type, or connectors that are bonded together.

As used herein, adapted for engaging, engagement, engaging, or similar terms refers to complementary structures that may align, mesh, mate, or rest near, against, or within each other. Exemplary structures include the connectors described above.

An exemplary apparatus according to the invention is shown in the figure. In the illustrated embodiment (see FIGS. 1 and 2), manifold assembly 10 may include one or more platforms. In a preferred embodiment of the invention, manifold assembly 10 includes a first platform 11 adapted to receive at least one container 20 suitable for holding a particulate matter-containing fluid, a second platform 12 adapted to receive a first portion 30 of a fluid processing or filter assembly, and a third platform 13 adapted to receive a second portion 40 of a fluid processing or filter assembly. Second portion 40 of the filter assembly is adapted to matingly engage a network or plurality of conduits 50 in fluid communication with a pressure differential generator 60, such as a pump (see FIG. 2). In a preferred embodiment of the invention, container 20, first portion 30, and second portion 40 matingly engage (see FIG. 7), preferably forming a liquid tight seal, and preferably establishing a fluid flow path between container 20 and fluid receptacle 90, i.e., through first portion 30 and second portion 40 (comprising a filter assembly housing a porous arrangement 71) and conduits 50.

One or more of platforms 11, 12, and 13 are moveable in respect to one another so that container 20, first portion 30, and second portion 40 engage one another sufficiently to establish a fluid flow path between the container 20 and the pressure differential generator 60. The manifold assembly 10 may also include a platform 14 adapted to receive one or more microscope slides 15 in cavities or the like and adapted to slidingly engage platform 13.

Each of the components of the invention will now be described in more detail below.

The source and receiving containers 20 which may be used in the biological fluid processing assembly may be constructed of any material compatible with particulate matter-containing fluids, such as biological fluids. A wide variety of these containers are already known in the art. Exemplary materials are described in U.S. Pat. Nos. 5,139,031; 5,301,685; and 5,471,944, each incorporated herein in its entirety by reference. Exemplary materials include but are not limited to a polyolefin, a polyurethane, a polyester, a polycarbonate, PVC, or plasticized PVC (e.g., with diotylphthalate, diethylhexylphthalate, or trioctyltrimelliate).

The configuration and materials used to make the container 20 can be any of a variety of materials, shapes, and sizes. For example, the container can be constructed of any material compatible with the fluid to be processed. It will be appreciated that the container and the assembly of the side walls to the bottom wall can be any conventional assembly. In a preferred embodiment of the invention, bottom wall 22 is a conical member (see FIG. 7).

Figure 2:
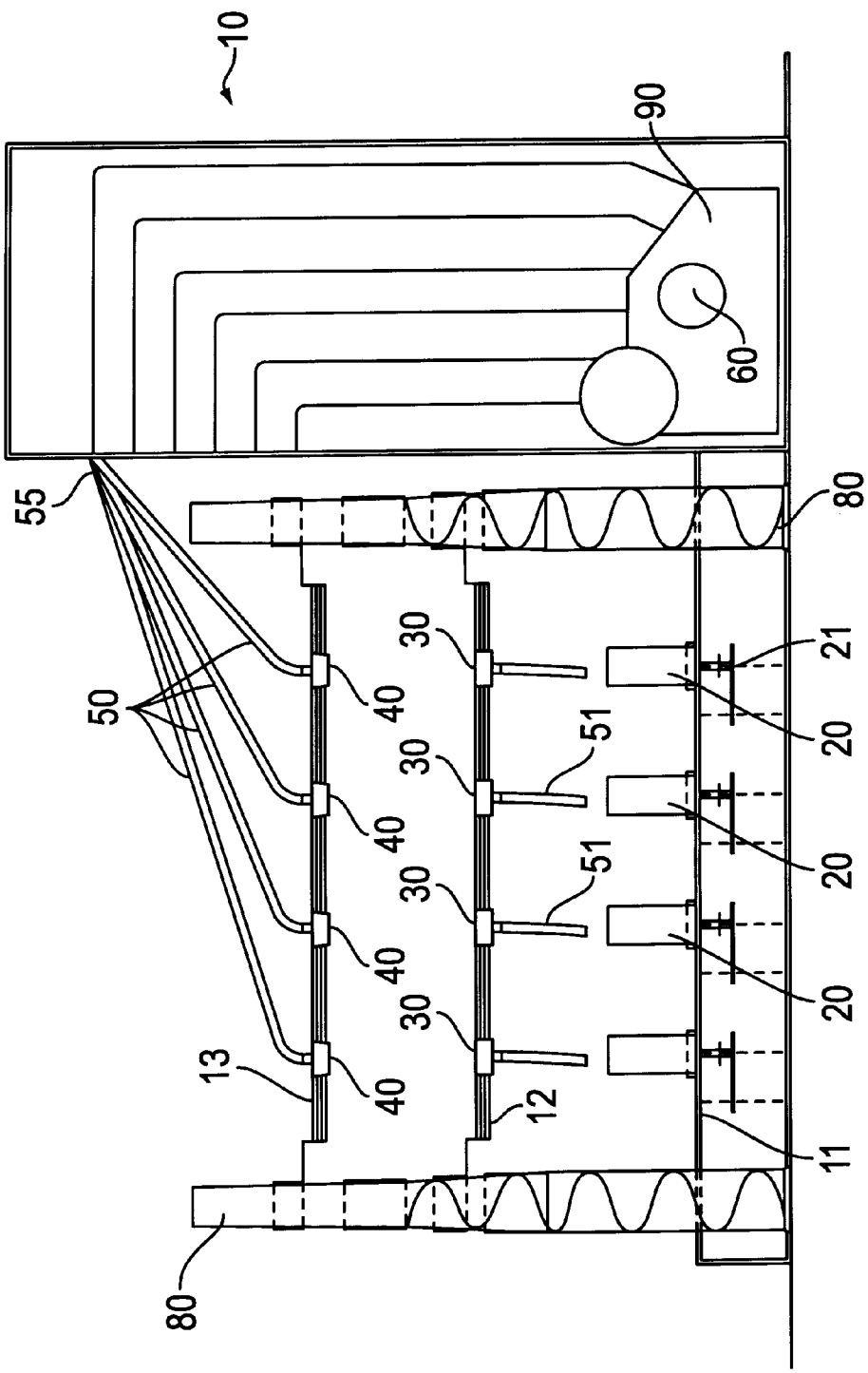
FIG. 2 is a side elevational view of the manifold assembly shown in FIG. 1.
Figure 3:
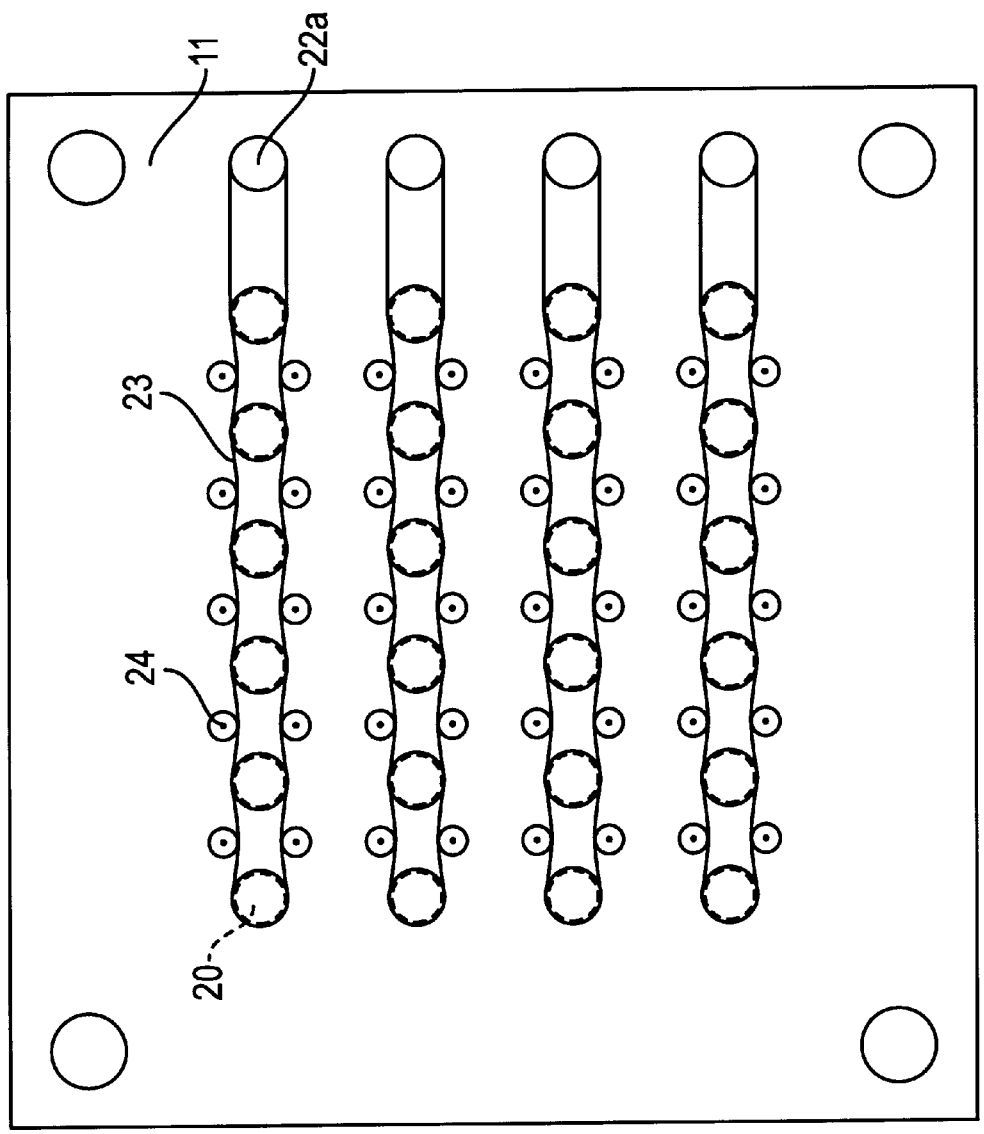
FIG. 3 is a top plan view of the lower or bottom platform 11.

As shown in FIGS. 2 and 3, container 20 seated on platform 11 may be configured or adapted to engage a stirring assembly 21. In a preferred embodiment of the invention, stirring assembly 21 engages a dispersing element 51 positioned within the container or the container 20 so that upon activation of the stirring assembly, dispersing element 51 moves in relation to container 20. In accordance with the invention, stirring assembly 21 may include a variety of structures and subassemblies. In the embodiment illustrated in FIG. 1, stirring assembly 21 includes a motor 22a that moves a belt 23 that movably engages a portion of container 20 so that container 20 rotates. Pins 24 are shown as exemplary of structures used to position the belt 23. Alternatively, belt 23 may engage a pin or the like that engages and rotates dispersing element 51 (see, for example, FIG. 7).

Figure 7:
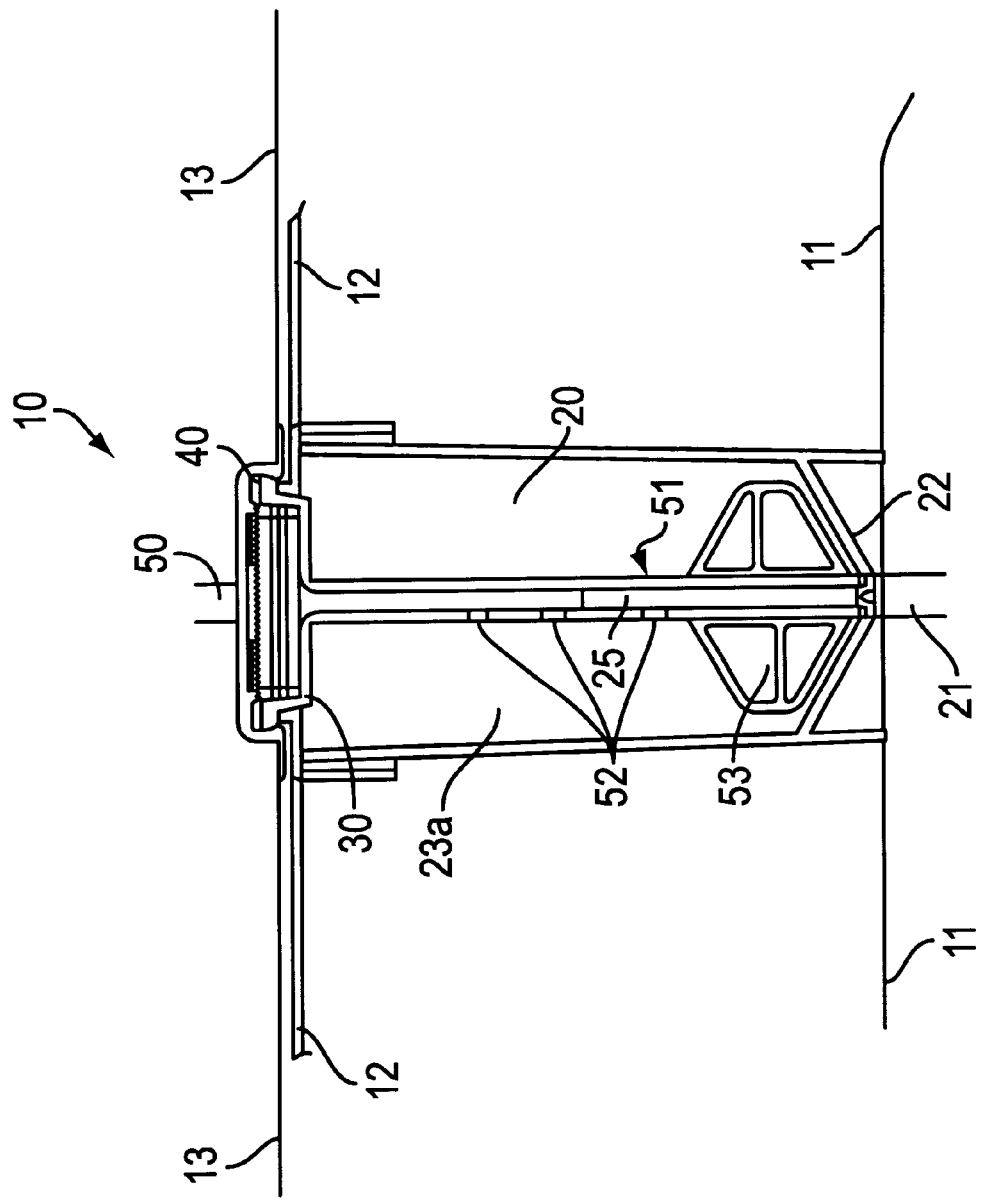
FIG. 7 is a side vertical sectional view of the closed processing assembly.

In accordance with another embodiment of the invention, dispersing element 51 may include hollow tube 25 and/or at least one projection or fin 53 or the like (see FIG. 7). Typically, hollow tube 25 includes one or more holes or apertures 52 that allows fluid in the container to pass into the tube 25. In a preferred embodiment of the invention, hollow tube 25 is rotatable and fin 53 stirs the liquid specimen, and in a most preferred embodiment, disperse cells and/or particulate matter, and/or to disrupt any large particulate matter such as mucoid bodies.

Manifold assembly 10 includes a second or intermediate platform 12 adapted to receive a first portion 30 of a fluid processing assembly 70. As described in more detail below, the fluid processing assembly 70 comprises first portion 30 and second portion 40. First portion 30 may be variously configured, and is preferably configured to receive a porous filter arrangement 71, described in more detail below. In the embodiment of the invention in which container 20 rotates to stir the fluid, first portion 30 also includes a tube or conduit 25 or the like that extends from first portion 30 into fluid in container 20.

Manifold assembly 10 includes a third or top platform 13 adapted to receive second portion 40 of fluid processing assembly 70. Second portion 40 may be variously configured, and is preferably configured to releasably receive a porous filter arrangement 71, described in more detail below. Second portion 40 is also adapted to engage conduit 50.

In accordance with the invention, a sample is collected using conventional techniques, e.g., by collecting urine or other biological fluid in a specimen container, or by placing a swab or brush in a suitable fluid in the specimen container (as is typical for a PAP smear). In a most preferred embodiment of the invention, the specimen or sample is collected in a sample container having the design and function as described above and below. The sample container is then capped with a cover, such as first portion 30, a portion of which is suitable for engaging a porous filter arrangement 71. The typical cover includes a central recessed portion adapted to receive the filter. In some embodiments of the invention, the central recessed portion also communicates with or engages a hollow tube that extends into the specimen container. Optionally, a portion of the tube may include a stirring or dispersing element.

In a preferred embodiment of the invention, a specimen cup includes a chamber for collecting a liquid specimen, and a cover that establishes fluid communication between the chamber and a filter assembly or module for separating particulate matter from the fluid and collecting the separated particulate matter in a collection zone. In a most preferred embodiment of the invention, the separated particulate matter is collected in a monolayer on the collection zone. A preferred embodiment of the invention also includes a cover having a hollow tube that provides fluid communication between the interior of the collection container and the filter assembly. More preferably, the hollow tube includes means for mixing the specimen and/or dispersing the particulate matter in the specimen.

In accordance with the invention, specimen container 20 includes any container suitable for holding a fluid, preferably a biological fluid. The typical container includes side walls and bottom wall 22 that, in combination, provide a chamber 23a for collecting, holding, or storing a fluid See FIG. 7. Typical fluids include, but are not limited to biological fluids, such as body fluids, waste water fluids, or the like. Typical body fluids include urine or other biological fluids, such as blood, cerebrospinal fluid (CSF), bronchial lavage, sputum or fine needle aspirates.

An apparatus according to the invention includes a top platform 13 having one or more second portions 40 positioned therein. As previously noted, second portion 40 is adapted to engage a portion of the specimen container cover 30. In a preferred embodiment of the invention, second portion 40 defines a cavity adapted for retrieving or engaging a filter as described below. In a most preferred embodiment, second portion 40 of the filter assembly matingly and removably engages a portion of the cover, and in mating engagement, forms a chamber adapted to position and accommodate a filter assembly. In accordance with the invention, the filter assembly and housing provide at least two fluid flow paths through the housing.

In another embodiment of the invention, second portion 40 includes a fitting or the like adapted to fittingly engage a conduit 50. In a preferred embodiment, conduit 50 is in fluid communication with a pump 60 or the like. In this embodiment of the invention, the various structures provide a fluid flow path from the specimen container, through the particulate matter separation chamber, and away from the specimen container.

Figures 1, 4A:
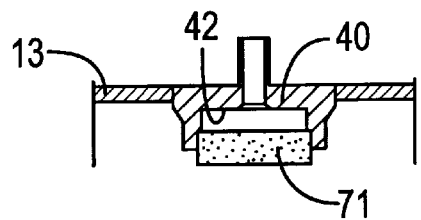
Figures 2, 4A:
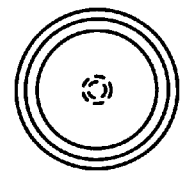
Figures 1, 4B:
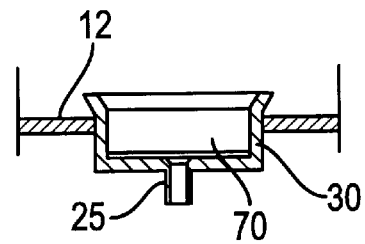
Figures 2, 4B:
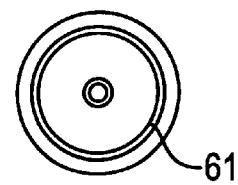
Figure 4C:
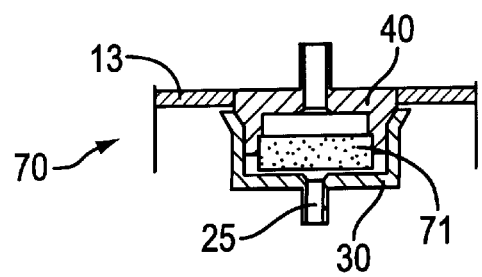
FIG. 4C is a vertical sectional view through the assembled filter assembly of FIGS. 4A-1, 4A-2, 4B-1 and 4B-2.
Figure 5:
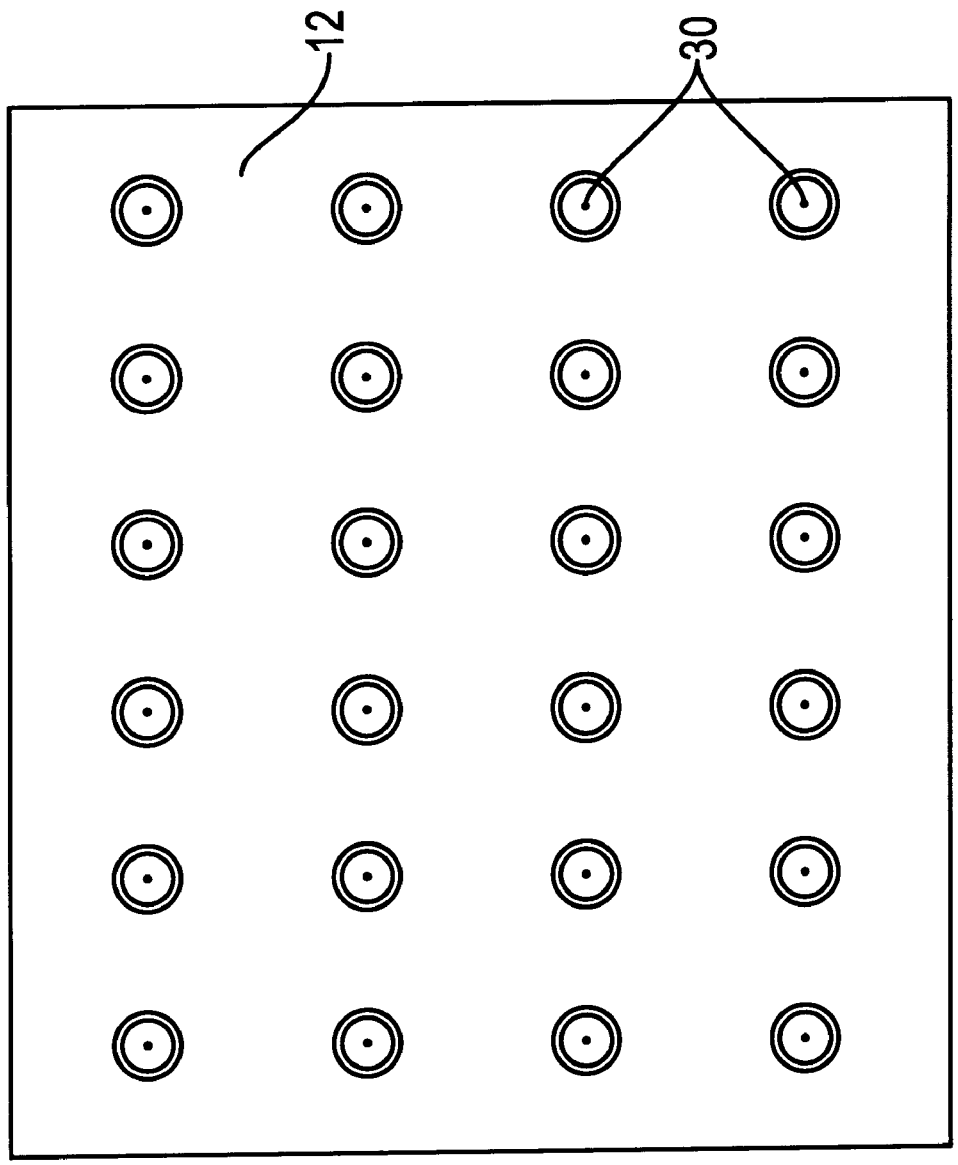
FIG. 5 is a top plan view of intermediate platform 12 and first portion 30.
Figure 6:
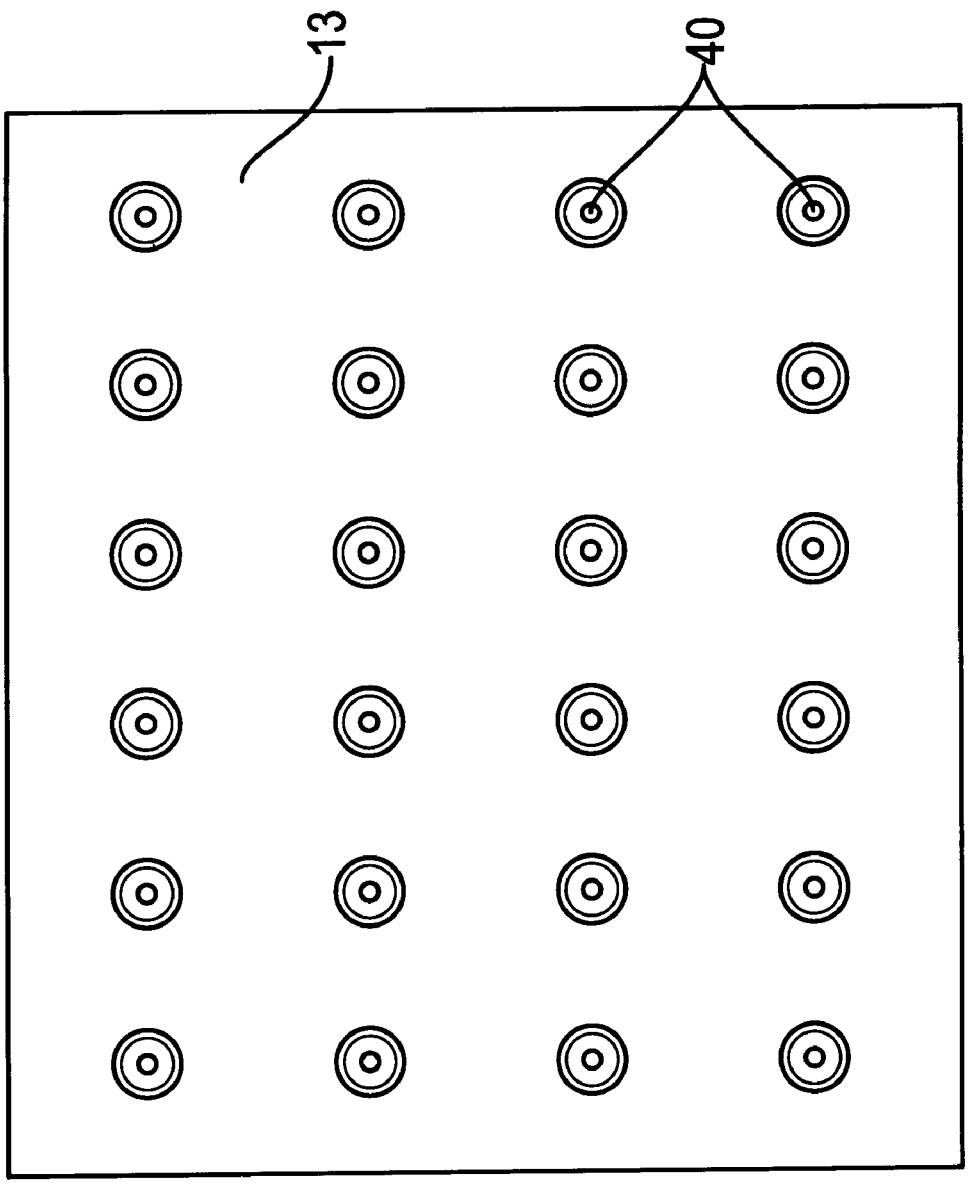
FIG. 6 is a top plan view of top platform 13 and second portion 40.

As noted above, an upper portion of the cover and a lower portion of the filter head assembly form a housing and chamber. The housing and chamber may be variously configured. Exemplary configurations are shown in FIGS. 4A-1 through 4C. In a preferred embodiment, the chamber is defined by a base portion 30 formed in part from or engaged with the cover of the specimen container 20.

Base portion 30 also defines a well suitable for seating a porous filter arrangement 71. The well may be provided with a channel or the like communicating with hollow tube 25. The well may be an integral structure of base 30, or may be a separate structure. In a preferred embodiment of the invention, the well is a separate structure that is capable of rotating in the platform recess. In order to achieve ease of centrifugal rotation while maintaining a fluid-tight assembly, the well may matingly engage platform 12 through a tongue and groove arrangement, visible in FIG. 7.

In accordance with the invention, the filter assembly chamber is configured to receive a porous arrangement 71 having a particulate matter collection site adapted to collect particulate matter as fluid containing the particulate matter passes through the chamber. Suitable porous arrangements, porous media, filters, filter assemblies and collection sites are known to those skilled in the art. Preferred examples of each are disclosed in U.S. Pat. No. 5,301,685; U.S. Pat. No. 5,471,994; provisional application No. 60/054,799, filed Aug. 5, 1997; provisional application No. 60/056,445, filed Aug. 25, 1997; provisional application No. 60/064,271, filed Nov. 4, 1997; and Ser. No. 08/963,873, filed Nov. 4, 1997. Each of these patents and applications are hereby incorporated by reference in their entirety.

Porous arrangement 71 may be positioned across a fluid flow path, the collection site communicating with hollow tube 25. The porous arrangement 71 within the matter separation chamber is preferably adapted to define at least one fluid flow path having first and second branches, the first branch extending through the collection site and the second branch bypassing the collection site.

In a preferred embodiment, the invention includes a porous arrangement 71 having a first porous medium suitable for preventing the passage of matter therethrough, and a second porous medium suitable for allowing fluid to pass therethrough. The second porous medium may or may not be capable of removing particulate matter from the fluid, a design choice according to the needs of a particular device. In a preferred embodiment, the first porous medium is suitable for capturing or collecting particulate matter, and even more preferably, capturing or collecting solid matter in a uniform or single layer. A preferred embodiment also includes a second porous medium which is suitable as a support for the first porous medium.

The nature of the material used to make the porous media, the compatibility of the materials chosen for the porous media with one another and with the liquid to be processed are all factors to be considered in selecting a particular material for a porous medium for a given application.

The first porous medium and the second porous medium may be positioned in any fashion that functions as described herein. As one skilled in the art will recognize, the porous arrangement may be variously configured and positioned as needed to achieve a particular result. For example, the first and second porous media may be separate, spaced apart media; the two media can be laminated together; the first medium can be integral with or removably engaged with the second porous medium; or the collection element may comprise a zone of higher density which mimics the function of the first porous medium as described above, and zone of lower density which mimics the function of the second porous medium as described above. Choice of these various configurations are well within the skill of practitioners in the art. Variations on the structure and composition of the porous arrangement will be described in more detail below.

As shown in FIGS. 4A-1 through 4C the filter assembly chamber 30 is preferably a two piece housing formed by a top portion 40 of a lower end of a filter head assembly, and a base portion 30 of a portion of a cover of the specimen container. In a preferred embodiment of the invention, top portion 40 releasably engages base portion 30; any housing configuration or assembly providing access to the porous arrangement 71 is suitable. Top portion 40 and base portion 30 may be connected or fastened to each other by any mating connection or means that provides a fluid tight fit, e.g., Luer-type (threaded or not threaded), screw thread-type, friction-type, a tapered mating connection, or snap fit (as illustrated).

In accordance with an embodiment of the invention, base portion 30 includes a seat with one or more spaced apart projections or the like. The projections are preferably of a size and shape sufficient to prevent porous arrangement 71 from flushly contacting the seat. In the illustrated embodiment, projections 61 are concentric rings (see FIG. 4B-1). Without intending to be limited to a particular theory of operation or function, projections break the surface tension between the porous arrangement and the seat so that, during use, when porous arrangement 71 is pulled away from seat, first porous medium does not remain in contact with the seat.

As noted above, top portion 40 engages base 30, and in combination, forms filter assembly chamber 70. Portion 40 may include a seat 42 or the like configured to engage the porous arrangement. In a preferred embodiment of the invention, the seat positions the porous arrangement in the top portion so that the porous arrangement does not move during use. In a most preferred embodiment of the invention, this seat includes a plurality of projections or posts (not shown) of a size, shape, and number to position the porous arrangement in the filter assembly chamber, to promote substantially even distribution of pressure against the porous arrangement, and to reduce or prevent compression of the porous arrangement that interferes with fluid flow through the porous arrangement. Alternatively or additionally, porous arrangement may include a serated portion that reduces or prevents compression of the porous arrangement.

Porous arrangement 71 may be positioned across a fluid flow path between the collection container 20 and the filtered fluid receptacle 90. The porous arrangement 71 within the matter separation chamber is preferably adapted to define at least one fluid flow path having first and second branches, the first branch extending through the collection site and the second branch bypassing the collection site.

As noted above, platforms 11, 12, and 13 are moveable in respect to each other. Although individual platforms may be stationary or moveable, the embodiment illustrated in FIG. 1 shows a stationary platform 11 and moveable platforms 12 and 13. In accordance with an embodiment of the invention, platforms 11, 12, and 13 are positioned with respect to one another by supports 80. Platforms may slidingly engage supports 80. In preferred embodiments of the invention, supports 80 are tapered or telescoping structures, but other configurations may be adapted to function as described above. In the configuration shown in FIG. 2, the manifold assembly is in its open position. In the fully closed position, the platforms are positioned so that container 20, first portion 30 and second portion 40 form a liquid tight seal, substantially as shown in FIG. 4C.

The first or specimen container platform 11 is preferably a substantially planar platform, disc, sheet, shelf, or the like. One preferred embodiment of the invention includes a sample container platform suitable for positioning and/or retaining one or more specimen containers. The platform typically includes one or more recesses, cavities, or sleeves adapted to accommodate at least one size of sample container. In a most preferred embodiment of the invention, the sample container platform includes at least two recesses for accommodating a least two different size sample containers. In accordance with the invention, the specimen container platform is movable to predetermined positions, including one or more positions that align a portion or portions of the platform adjacent to or in proximity to another element of the manifold apparatus, e.g., an intermediate platform.

In accordance with the invention, the intermediate platform 12 is movable, preferably adapted to slidingly engage the manifold assembly. In accordance with the invention, the microscope slide platform 14 is movable to a predetermined position, including one or more positions that align a portion or portions of the platform adjacent to or in proximity to another element of the manifold apparatus.

An apparatus according to the invention may also include one or more elements for altering differential pressure within the apparatus so that fluid can move through a portion of the apparatus. In accordance with the invention, the fluid may be either gaseous or liquid, depending on the use. For example, inducing a vacuum in a conduit in fluid communication with the sample container will draw liquid in the container through the filter assembly. It may be desirable to induce a positive pressure to return the liquid to the specimen container, or to move the filtered liquid to a disposal container or chamber. It may be desirable to clean or rinse a portion of a sub-assembly, e.g., a portion of the filter head assembly. In this embodiment of the invention, a pump or the like may move a rinse solution from a source container through a conduit to the filer head assembly. Included within the present invention are a variety of source containers, pressure differential generators, and conduits for establishing fluid communication between or to pre-selected elements of the apparatus.

Movement of a fluid through the system may be effected by maintaining a pressure differential between a source of fluid and a destination of the fluid. Exemplary means of establishing this pressure differential may be by applying pressure to any part of the system on the inlet side of the housing (e.g., the collection cup); applying a vacuum to any part of the system on the outlet side of the housing (e.g., the syringe); or any form of pump, such as an autovial spunglass filter (manufactured by Genex Corporation); gravity head; or a flexible, collapsible container, such as a specimen container, which may be squeezed to force fluid through the matter collection apparatus and into the syringe. In a preferred embodiment of the invention, a syringe draws fluid from a collection cup through the housing.

A method according to the invention may be described with reference to FIGS. 1 and 2, where the components are shown in a preferably vertical arrangement, with the source containers 20 at the lowest point. Once a sample containing particulate matter is placed in container 20, platforms 11, 12, and 13 are moved in relation to each other so that the filter assembly housing is closed, e.g., such as that shown in FIG. 4C. Closing the filter assembly housing establishes a fluid flow path through the system, e.g., between the source container and the filtered fluid receptacle. In a preferred embodiment, stirring assembly 21 is activated, either manually or mechanically, to rotate the specimen container 20 in relation to dispersing element 51. In the illustrated embodiment, the dispersing element is stationary and the container 20 rotates.

After a predetermined interval, the stirring assembly is stopped and, in the illustrated embodiment, pump 60 is activated to creates a vacuum sufficient to draw fluid from the source container 20 into tube 25, and through filter assembly 71. Filtered or processed fluid then passes from the filter assembly housing into conduits 50 of the manifold assembly, through one or more junctions 55 where the number of conduits is reduced, and into a filtered fluid receptacle 90.

As a result of the fluid passing through the system, particulate matter is collected on a collection site of filter assembly 71. By moving platform 13 to an open position, the collection site is exposed. Platform 14 containing microscope slides or the like may then be positioned adjacent to the collection site for each filter assembly. Platform 14 is then moved so that each microscope slide contacts its corresponding collection site. Such contact transfers the collection site, e.g., a membrane containing the filtered particulate matter, to the microscope slide.

After the membrane is transferred to the microscope slide, visual, diagnostic, or other cytological examinations may occur, as are well known to practitioners in the art. For example, particulate matter may be transferred to the microscope slide and subjected to visual or microscopic examination, or an infra red reader.

While the invention has been described in some detail by way of illustration and example, it should be understood that the invention is susceptible to various modifications and alternative forms, and is not restricted to the specific embodiments set forth. It should be understood that these specific embodiments are not intended to limit the invention but, on the contrary, the intention is to cover all modifications, equivalents, and alternatives falling within the spirit and scope of the invention.

What is claimed is:

1. An apparatus for processing particulate matter-containing fluid comprising:

a plurality of source containers for containing said fluid;

a manifold assembly in fluid communication with said source containers;

means for moving said fluid upwardly out of said source containers and into said manifold assembly; and a filter assembly associated with each of said source containers for removing particulate matter from said fluid, each of said filter assemblies being positioned at the top of its respective source container and in the fluid flow path between said source container and said manifold assembly.

2. The apparatus of claim 1 wherein the manifold assembly provides fluid communication between the source containers and a receptacle for processed fluid.

3. The apparatus of claim 1 wherein each of said filter assemblies comprises separable upper and lower housing portions and a filter within said housing portions for collecting said particulate material.

4. The apparatus of claim 3 further comprising a movable slide support adapted to hold microscope slides and position a slide adjacent each of said filters when said upper and lower housing portions are separated so that particulate material can be transferred from each filter to its respective slide.

5. The apparatus of claim 4 further comprising a controller for activating and positioning portions of the apparatus.

6. The apparatus of claim 3 wherein a portion of each of said filters collects particulate matter on a collection site.

7. An apparatus for removing particulate matter from a fluid comprising:

a first platform having at least one source container positioned thereon;

a filter assembly associated with said source container, said filter assembly comprising separable first and second housing portions and a filter within said housing portions for collecting said particulate material;

a second platform supporting said first housing portion in fluid communication with said source container;

a third platform supporting said second housing portion in sealed relation to said first housing portion;

a manifold assembly in fluid communication with said second housing portion;

means for moving said fluid from said source container through said filter assembly and into said manifold assembly; and a fourth platform adapted to hold at least one microscope slide and movable to position said slide adjacent said filter when said housing portions are separated so that particulate material can be transferred from said filter to said slide.

8. The apparatus of claim 7 wherein said platforms are relatively movable to separate said first housing portion from said source container and separate said second housing portion from said first housing portion, and vice versa.

9. The apparatus of claim 8 wherein said second platform is positioned above said first platform, said third platform is positioned above said second platform, and said fluid moves upwardly through said filter assembly.

10. The apparatus of claim 9 comprising a plurality of source containers on said first-platform and a filter assembly associated with each of said source containers, the first housing portion of each of said filter assemblies being supported on said second platform and the second housing portion of each of said filter assemblies being supported on said third platform, and wherein said fourth platform is adapted to hold a plurality of slides and position each of said slides adjacent a respective filter to accept particulate matter therefrom.

11. The apparatus of claim 7 comprising a plurality of source containers on said first platform and a filter assembly associated with each of said source containers, the first housing portion of each of said filter assemblies being supported on said second platform and the second housing portion of each of said filter assemblies being supported on said third platform, and wherein said fourth platform is adapted to hold a plurality of slides and position each of said slides adjacent a respective filter to accept particulate matter therefrom.

12. The apparatus of claim 11 wherein said platforms are relatively movable to separate said first housing portions from said source containers and separate said second housing portions from said first housing portions, and vice versa.

* * * * *